United States Patent [19]
Mason

[11] Patent Number: 5,183,065
[45] Date of Patent: Feb. 2, 1993

[54] DENTAL FLOSSING TOOL

[76] Inventor: Robert F. Mason, 10763 Hedda Pl., Cerritos, Calif. 90701

[21] Appl. No.: 675,869

[22] Filed: Mar. 27, 1991

Related U.S. Application Data

[63] Continuation-in-part of Ser. No. 353,592, May 18, 1989, abandoned, and Ser. No. 478,527, Feb. 12, 1990, abandoned.

[51] Int. Cl.$^5$ .............................................. A61C 15/00
[52] U.S. Cl. ..................................... 132/323; 132/324; 132/325
[58] Field of Search ............... 132/323, 324, 325, 326, 132/327

[56] References Cited

U.S. PATENT DOCUMENTS

| | | | |
|---|---|---|---|
| 1,210,205 | 12/1916 | Richardson | 132/324 |
| 1,480,101 | 1/1924 | Ogden | 132/324 |
| 1,608,212 | 11/1926 | Hochstadter | 132/326 |
| 1,955,428 | 4/1934 | Ladwig | 132/324 |
| 3,833,009 | 9/1974 | Bennington | 132/325 |
| 3,870,059 | 3/1975 | Bennington | 132/326 X |
| 3,908,678 | 9/1975 | Conn et al. | 132/325 |
| 3,924,647 | 12/1975 | Lindblad | 132/326 |
| 4,574,823 | 3/1986 | Uriss | 132/325 |
| 4,657,034 | 4/1987 | Koski | 132/324 |
| 4,660,584 | 4/1987 | Wofford | 132/325 |
| 4,901,742 | 2/1990 | Olson | 132/325 |

FOREIGN PATENT DOCUMENTS 1359802  7/1974  United Kingdom ............... 132/325

Primary Examiner—Robert P. Swiatek
Assistant Examiner—Nicolas D. Lucchesi
Attorney, Agent, or Firm—Robert M. Sperry

[57] ABSTRACT

An improved dental flossing tool comprising a single flossing rod or tool is provided, containing a supply of dental floss therein and from which a strand of floss extends, and two hands are used, one to grip the flossing rod or tool, and the other to hold the free end of the floss strand at the proper angle and with the proper tension, with the second hand holding the free end of the floss strand. The floss tool of the present invention is preferably hollow, with a supply of dental floss mounted therein, and has a hollow, narrow tip through which the floss strand is routed internally to project from the end of the tip for use. A locking device is provided for selectively blocking the feeding of the floss strand in lengths which may be varied as desired and a restricting device is provided for restricting movement of the floss strand and for preventing moisture from entering the interior of the tool.

14 Claims, 2 Drawing Sheets

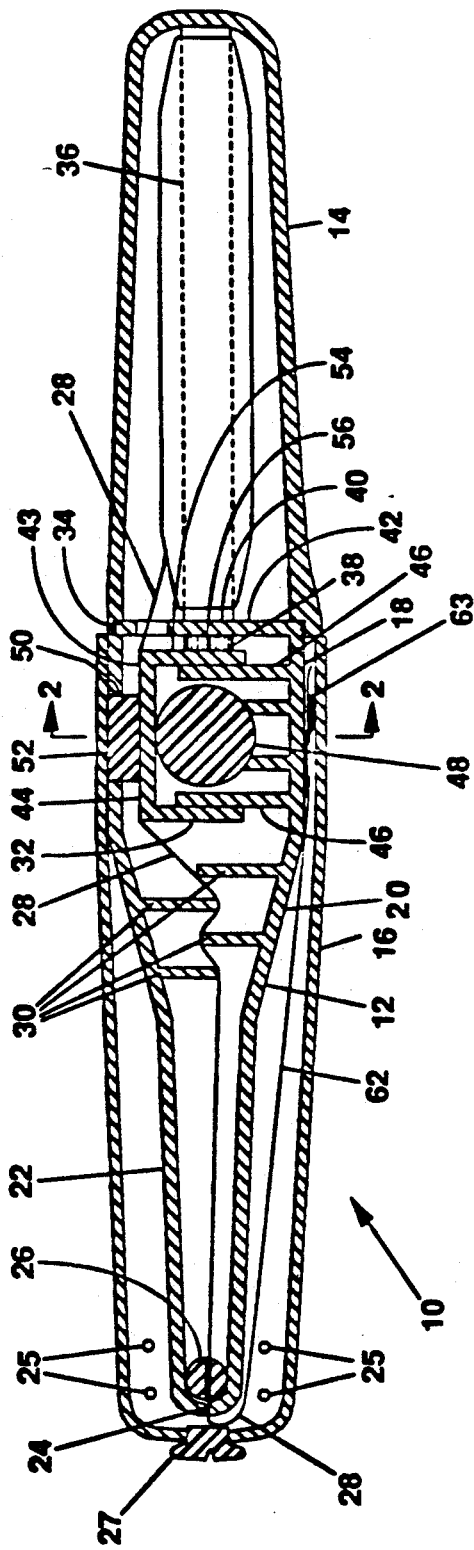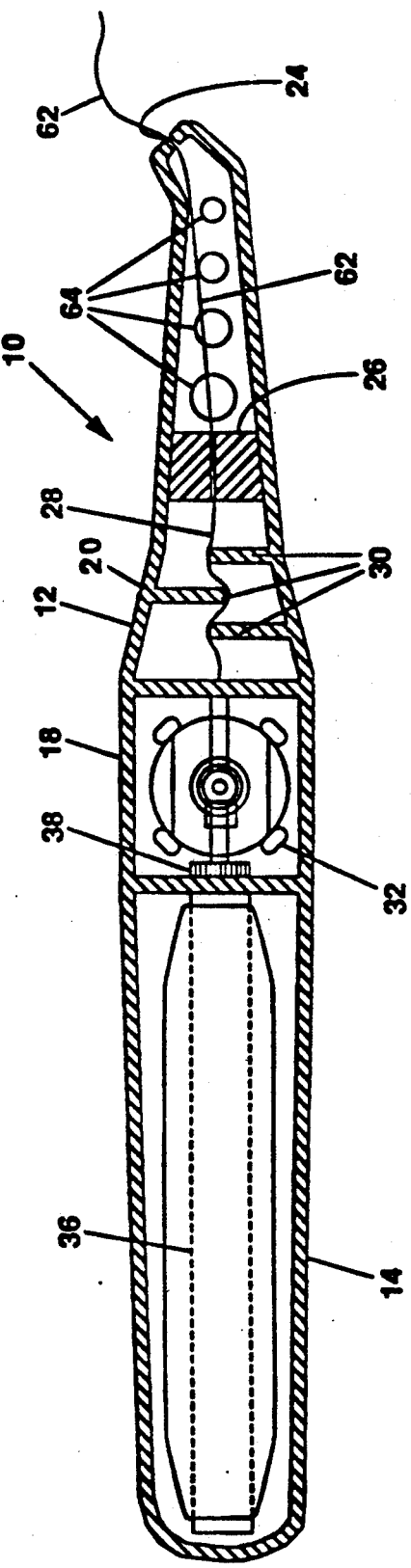

DENTAL FLOSSING TOOL

BACKGROUND

Related Cases

This application is a continuation-in-part of my previously filed patent applications Ser. No. 353,592, filed May 18, 1989, entitled "Tooth Flossing Instrument", and now abandoned, and Ser. No. 478,527, filed Feb. 12, 1990, entitled "Drying Mandrel For Flossing Tool", and now abandoned.

FIELD OF INVENTION

This invention relates to dental flossing instruments and the like.

PRIOR ART

It is well-known and accepted that the flossing of teeth is a desirable technique for dental health and for avoiding cavities and other problems with the teeth and gums. However, most people do not regularly floss their teeth, in part as a result of the difficulty and waste inherent in using conventional dental floss or dental tape dispensers and holding the floss or tape entirely with one's hands. However, unless the user washes their hands thoroughly, prior to the flossing operation, this handling of the floss often results in contamination of the floss and facilitates introduction of germs and other contaminants into the user's mouth which may result in infection and is certainly contrary to dental hygiene.

A number of two-pronged appliances have been proposed for holding dental floss and reference is made to the devices shown in U.S. Pat. Nos. 1,217,774; 2,233,936; 3,861,406 and 4,495,957. These tools stretch the floss across between the two prongs and are intended for use with one hand. However, the junction between adjacent teeth is rarely a complete straight line and it is, therefore, difficult to get the floss started between the teeth. Also, when such two-pronged tools are used with only one hand, the tension in the floss is preset and it is difficult to vary the tension or angle, as needed, for effective flossing. Furthermore, many of the two-pronged flossing tools have served merely as holders for the floss and have required that the user break off a length of floss with their hands and install it between the prongs of the tool for use. However, this still requires handling and possible contamination of the dental floss.

Some prior art dental flossing tools have been proposed which contain a reel or other supply of dental floss mounted on or inside of the tool and have included means for delivering a strand of floss to a single prong or tip with the intention that the user can grip the free end of the floss strand and hold the tool with the other hand to perform the flossing operation. However, many of these single tip flossing tools have provided no means for regulating the rate of removal of the floss strand from the tool. Thus, it is difficult or impossible to provide or regulate the tension of the floss strand, as needed, during the flossing operation. Other single tip flossing tools have provided means for regulating removal of floss from the tool which permit removal of floss only in predetermined lengths corresponding to complete revolutions of the floss spool. However, in practice, the user may wish to use different lengths of floss between respective pairs of teeth. This has not been possible with the dental flossing tools of the prior art, where the spool is used to stop the floss.

A further disadvantage of prior art dental flossing tools has been the fact that those tools which carry a supply of dental floss permit exposure of the floss to the atmosphere prior to use. However, dental flossing tools are generally used in bathrooms and the like where there is a high probability of the presence of germs and other contaminants, many of which are air-borne, and these germs, moisture and other contaminants can invade the interior of the tool through the hole where the floss exits. Thus, these tools allow such germs or other contaminants to enter into the floss supply and, especially if the floss supply is contained within the interior of the flossing tool, an ideal environment is provided for the growth of these germs and the like.

A search in the United States Patent Office has revealed the following:

| U.S. PAT. NO. | INVENTOR | ISSUED |
|---|---|---|
| 3,831,611 | Hendricks | Aug. 27, 1974 |
| 4,005,722 | Bragg | Feb. 1, 1977 |
| 2,872,929 | Rice | Feb. 10, 1959 |
| 4,434,807 | Husky | Mar. 6, 1984 |
| 4,232,688 | Day | Nov. 11, 1980 |
| 1,287,926 | Ecaubert | Dec. 17, 1918 |
| 2,180,522 | Henne | Nov. 21, 1939 |
| 4,050,470 | Miller | Sep. 27, 1977 |
| 4,379,177 | Bragg | Mar. 26, 1974 |
| 4,657,034 | Koski | Apr. 14, 1987 |
| 3,870,059 | Bennington | Mar. 11, 1975 |
| 1,210,205 | Richardson | Dec. 26, 1916 |
| 4,495,957 | Beggs et al | Jan. 29, 1985 |
| 4,337,767 | Yahata | Jul. , 1982 |
| 4,030,493 | Walters | Jun. , 1977 |
| 2,857,911 | Bennet | Oct. , 1958 |
| 4,809,692 | Nowacki et al | Mar. , 1989 |
| 3,695,264 | Laerel | Oct. , 1972 |
| 4,543,950 | Keys, Jr. | Oct. , 1985 |
| 4,819,628 | Berman | Mar. , 1963 |
| 4,881,540 | Pantaleon | May , 1989 |
| 2,917,045 | Schildvnecht | Dec. , 1959 |
| 4,597,398 | Chu | Jul. 1, 1986 |
| 1,608,212 | Hockstadler | Nov. 23, 1926 |
| 4,821,752 | Widlak | Apr. 18, 1989 |
| 3,847,168 | Schlegel | Nov. 12, 1974 |
| 3,915,178 | Zellers | Oct. , 1975 |
| 3,881,502 | Bennington | May , 1975 |
| 3,901,251 | Johnston | Aug. , 1975 |
| 4,495,957 | Beggs | Jan. , 1985 |
| 4,807,651 | Naydich | Feb. , 1989 |
| 3,885,579 | Navrat | May , 1975 |
| 1,524,273 (French) | Fernez | Apr. , 1960 |
| 2,652,128 (German) | Dragearwork | Dec. , 1977 |
| 193,720 (Sweden) | Motala | Jan. , 1965 |
| 2,336,879 (German) | Panta | Feb. , 1975 |
| 2,193,957 (British) | Brayshaw | Jun. , 1988 |

However, each of these references is subject to the limitations discussed above. Thus, none of the prior art dental flossing tools have been entirely satisfactory.

BRIEF SUMMARY AND OBJECTS OF INVENTION

In accordance with the present invention, a single flossing rod or tool is provided, containing a supply of dental floss therein and from which a strand of floss extends, and two hands are used, one to grip the flossing rod or tool, and the other to hold the free end of the floss strand at the proper angle and with the proper tension, with the second hand holding the free end of the floss strand. The floss tool of the present invention is preferably hollow, with a supply of dental floss mounted therein, and has a hollow, narrow tip through which the floss strand is routed internally to project from the end of the tip for use. Locking means are provided for selectively blocking the feeding of the floss strand in lengths which may be varied as desired and means are provided for preventing moisture and other contaminants from entering the interior of the tool.

Accordingly, it is an object of the present invention to provide an improved dental flossing tool.

Another object of the present invention is to provide an improved dental flossing tool which can be held in one hand, while the user holds the free end of the floss strand in their other hand to facilitate manipulating the floss strand between adjacent teeth and to vary the tension on the floss strand as desired during the flossing operation, and also being able to deliver more floss, as needed, with the floss strand between adjacent teeth, while in the process of flossing the teeth.

An additional object of the present invention is to provide an improved dental flossing tool containing a supply of dental floss and having means to regulate withdrawal of the strand of dental floss from the tool to permit withdrawal of substantially any desired length of floss.

An additional object of the present invention is to provide an improved dental flossing tool containing a supply of dental floss therein and having means for preventing exposure of the strand of dental floss prior to dispensing the strand from the tip of the tool.

A further object of the present invention is to provide an improved dental flossing tool containing a supply of dental floss therein and having means for preventing moisture, germs and other contaminants from entering into the floss contained within the tool.

A further object of the present invention is to provide an improved dental flossing tool having means for preventing moisture and other contaminants from entering the interior of the tool.

A specific object of the present invention is to provide an improved dental flossing tool comprising a single flossing rod or tool containing a supply of dental floss therein and from which a strand of floss extends, and two hands are used, one to grip the flossing rod or tool, and the other to hold the free end of the floss strand at the proper angle and with the proper tension, with the second hand holding the free end of the floss strand. The floss tool of the present invention is preferably hollow, with a supply of dental floss mounted therein, and has a hollow, narrow tip through which the floss strand is routed internally to project from the end of the tip for use. Locking means are provided for selectively blocking the feeding of the floss strand in lengths which may be varied as desired and for preventing moisture and germs from being drawn into the interior of the tool by a length of floss extending out of the tip of the tool.

These and other objects and features of the present invention will be apparent from the present invention, taken with reference to the figures of the accompanying drawings.

BRIEF DESCRIPTION OF THE DRAWINGS

FIG. 1 is a vertical section through a dental flossing tool embodying the present invention;

FIG. 4 is a vertical section through the tip of an alternative form of the dental flossing tool of FIG. 1.

DETAILED DESCRIPTION OF THE INVENTION

Figure 2:
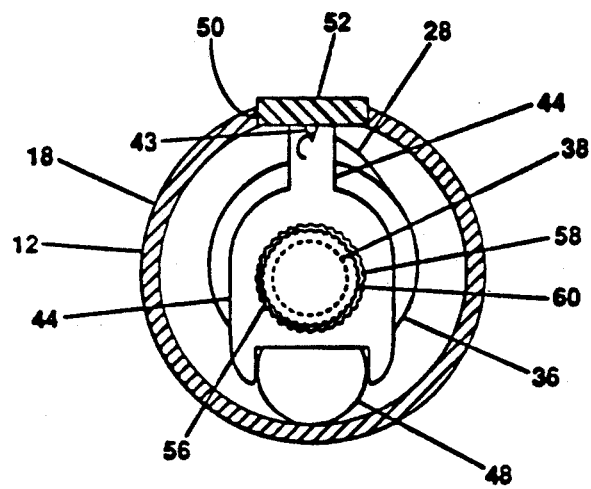
FIG. 2 is a transverse section through the dental flossing tool of FIG. 1, taken on the line 2—2 of FIG. 1.

In that form of the present invention chosen for purposes of illustration in FIG. 1, a dental flossing tool, indicated generally at 10, is shown having a main housing 12, a rear housing 14 and a cap 16. The main housing 12 has a generally cylindrical portion 18 with a tapered portion 20 projecting from the forward end of the cylindrical portion 18 and has a slender, elongated tip 22 projecting forwardly from the tapered portion 20. The tip 22 has an opening 24 formed at the extreme forward end thereof and an apertured resilient plug 26 is mounted inside the tip 22 immediately adjacent the opening 24 and is formed to permit passage of a strand 28 of dental flossing material through or about the apertured resilient plug 26 to be dispensed through opening 24 of tip 22. Within the tapered portion 20, the strand 28 of dental floss passes through a plurality of interfitting stationary teeth 30, which provide frictional resistance to movement of the strand 28. Also, suitable locking means, indicated generally at 32, are mounted within the cylindrical portion 18 of the main housing 12 to prevent undesired movement of the floss strand 28, as more fully described below.

The rear housing 14 is releasably secured to the main housing 12 by suitable means, such as threads 34 and contains a spool 36 of dental flossing material having a shaft 38 which projects beyond the forward end of the rear housing 14 and into an opening 40 formed in the forward end 42 of the rear housing 14. From the spool 36, the strand 28 of the dental flossing material passes forward from the main housing 12 and, thence, passes through a slot 43 in the top of piston 44, as best seen in FIG. 2, and passes between the intermeshing stationary teeth 30 to pass through the apertured resilient plug 26 and out through opening 24 of tip 22 for use.

Figure 3A:
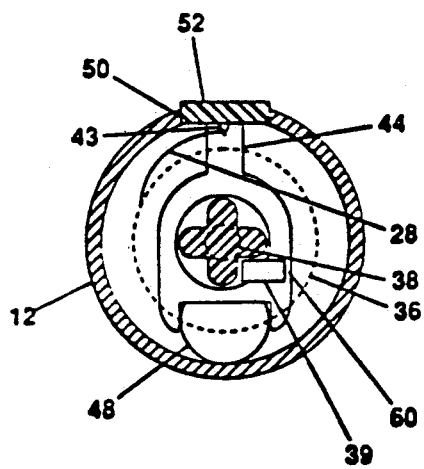
FIG. 3A is a view, similar to that of FIG. 2, showing an alternative form of the locking means of the dental flossing tool of FIG. 1.
Figure 3B:
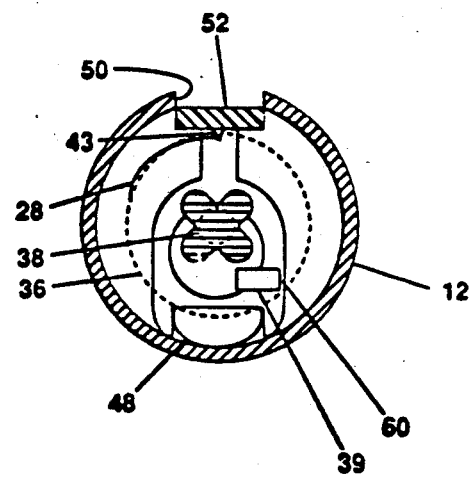
FIG. 3B is a view, similar to that of FIG. 3A, showing the locking means of FIG. 3A in its unlocked position.

Within the cylindrical portion 18 of the main housing 12, the locking means 32 comprises a generally U-shaped piston 44 which is slidable on suitable guide members 46 and which is normally urged to its locking position by resilient means, such as rubber ball 48. An opening 50 is formed in the cylindrical portion 18 of the main housing 12 and a resilient seal 52 serves to seal the opening 50 to prevent atmospheric moisture from entering the housing 12 and, if desired, may be sufficiently flexible to cause movement of the piston 44 against the action of the resilient means 48. The strand 28 of dental floss passes through slot 43 formed in the piston 44, but is out of contact with the seal 52. However, the rear leg 54 of the piston 44 is formed with an opening 56 which receives the shaft 38 of the spool 36 of dental floss. Resilient means 48 normally urges the edge of the opening 56 to bear against shaft 38 which causes frictional engagement of the piston 44 with the shaft 38 and, hence, serves as a brake to prevent undesired rotation of the shaft 38 and spool 36 to prevent undesired movement of the strand 28 of dental floss. Moreover, if desired, shaft 38 and opening 56 may be provided with mating serrations, as seen at 58 and 60 in FIG. 2, to cause the edge 60 of opening 56 to positively lock the shaft 38 against rotation. Alternatively, either of the edges 58 or 60 may be provided with a friction-enhancing coating, such as rubber. Furthermore, as seen in FIGS. 3A and 3B, the shaft 38 may be formed with a cruciform shape and a stud 39 is carried by the piston 44 and, when the piston 44 is urged by resilient means 48 into its normal locking position, stud 39 will engage the cruciform shaft 38, as seen in FIG. 3A, and will serve to prevent rotation of the shaft 38 and, consequently, will prevent movement of the strand 28 of dental floss. However, when the piston 44 is pushed inward, against the action of the resilient means 48, stud 39 will disengage from the shaft 38, as seen in FIG. 3B, to permit free rotation of the shaft 38 and, hence, will allow any desired length of the strand 28 of dental floss to be withdrawn from the spool 36. Obviously, if desired, other suitable braking means could be provided between the edge 60 of opening 56 and the shaft 38. If desired, the cap 16 may be provided with a plurality of openings, as seen at 25 in FIG. 1, to permit air to enter the interior of the cap 16 to ventilate the tip 22 of the dental flossing tool 10. Also, if desired, a pad 27 containing antiseptic material may be mounted within the cap 16 to engage the tip 22 of the tool 10 to aid in preventing germs and the like from contaminating the tip 22 and exposed portion 62 of the strand 28 of dental floss.

In use, the rear housing 14, containing a spool 36 of dental flossing material is secured to the main housing 12 of the dental flossing tool 10 so that shaft 38 of the spool 36 projects through opening 40 in the forward wall 42 of the rear housing 14 and projects into opening 56 of the U-shaped piston 44. The strand 28 of dental floss, from the spool 36, is passed through slot 43 in the top of piston 44 and seal 52 and is threaded between the interfitting stationary teeth 30 and passes through or about the apertured resilient plug 26 to project out of opening 24 in tip 22 of the dental flossing tool 10. To perform the flossing operation, the user holds the dental flossing tool 10 in one hand and, with the other hand, grasps the free end 62 of the strand 28 of dental floss. The user then presses one finger against the resilient seal 52 to press the U-shaped piston 44 inward against the urging of resilient means 48, causing the opening 56 of piston 44 to release the shaft 38 of the spool 36 of dental floss and releasing the locking action of piston 44. The user may then pull the free end 62 of the strand 28 of dental floss to withdraw any desired length from opening 24 of tip 22 of the tool 10. When the strand 28 of dental floss is at the desired length, the user removes their finger from the resilient seal 52, which allows resilient means 48 to urge piston 44 to its locking position, wherein the edge 60 of opening 56 engages the shaft 38 of spool 36 to prevent additional movement of the spool 36. Thus, the resilient means 48 causes piston 44 to lock both shaft 38 of the dental floss supply spool 36 to prevent undesired movement of the spool 36 of dental floss. Holding the free end 62 of the dental floss strand 28 in one hand and holding the dental flossing tool 10 in the other hand, the user may then freely manipulate the strand 28 of dental floss into the recesses between adjacent teeth and can vary the tension on the exposed portion of the strand 28 substantially as desired to properly perform the flossing operation.

Upon completion of the flossing operation. The free end 62 of the dental floss strand 28 is severed by suitable cutting means, such as that seen at 63 in FIG. 1. When this is done, the locking means 32 will prevent undesired movement of the strand 28 of dental floss and the interfitting stationary teeth 30 will frictionally assist in retarding movement of the floss strand 28. At the same time, the resilient plug 26 will press against the strand 28 of floss to prevent moisture, germs and other contaminants from entering through openging 24 into the interior of the tool 10. This prevents possible contamination of the strand 28 of dental floss contained within the tool 10 and assures the sterility of the strand 28 of dental floss for future flossing operations. To prevent contamination of the exposed portion 62 of the strand 28 of dental floss, the cap 16 can be formed to frictionally engage and seal against the outer surface of the cylindrical portion 18 of the main housing 12 to prevent exposure of the tip 22 of the dental flossing tool 10 and the free end 62 of the dental floss strand 28 from exposure to the atmosphere.

FIG. 4 shows an alternative form of the dental flossing tool 10 in which the tip 22 is provided with one or more openings 64 and the apertured resilient plug 26 is mounted between the openings 64 and the rear end of the elongated tip 22, for example, at the junction of the tip 22 with the tapered portion 20 of the housing 12. When it is likely that the exposed dental floss 62 may become wet, as when the dental flossing tool 10 is used in a shower, this form of the dental flossing tool 10 serves to facilitate drying of exposed portion 62 of the strand 28 of dental floss by allowing air to enter the tip 22 through the openings 64, while the resilient plug 26 still serves to prevent moisture and other contaminants from passing into the interior of the housing 12 to dampen and possibly contaminate the strand 28 of dental floss and the supply of dental floss carried by spool 36. Alternatively, if the dental floss carried by the spool 36 is dry, the openings 64 will permit water to enter the tip 22 to dampen the exposed portion 62 of the strand 28 of dental floss, while resilient plug 26 will prevent the moisture from entering the housing 12 to dampen and possibly contaminate the supply of dental floss carried by the spool 36 within the housing 12. Since the openings 64 permit air and water to enter and flush through the tip 22, the cap 16 may or may not be used for protection of the tip 22 during storage, as a matter of choice.

Obviously, numerous other variations and modifications can be made without departing from the spirit of the present invention. Therefore, it should be clearly understood that the forms of the present invention described above and shown in the figures of the accompanying drawings are illustrative only and are not intended to limit the scope of the present invention.

What is claimed is:

1. A dental flossing tool comprising:
   an elongated hollow handle portion having a single hollow tip projecting from one end of said handle portion,
   a supply of dental floss mounted in said handle portion,
   means for feeding said dental floss through said tool without exposure of said floss to air outside of said tool and for preventing exposure of said floss prior to said floss exiting said tip,
   resilient means substantially enclosed within said tip so that said tip extends beyond said resilient means and serving to prevent moisture from entering said tool while allowing said floss to exit from said too, and locking means located within said tool for selectably permitting removal of said floss from said supply in infinitely variable locked lengths.

2. The dental flossing tool of claim 1 further comprising:
means for retarding movement of said floss having a plurality of interfitting stationary teeth.

3. The dental flossing tool of claim 1 wherein said locking means comprises:
a spool carrying said supply of dental floss,
a piston moveable between a locked position frictionally engaging said spool and an unlocked position out of engagement with said spool, and
resilient means normally urging said piston to said locked position.

4. The dental flossing tool of claim 3 wherein:
said resilient means is a rubber ball.

5. The dental flossing tool of claim 3 further comprising:
an opening formed in said tool adjacent said piston, and
a resilient means sealing said opening to prevent passage of moisture into said tool and sufficiently flexible to permit a user to apply pressure through said seal to move said piston.

6. The dental flossing tool of claim 1 further comprising:
a spool containing said supply of dental floss,
said locking means including means releasably engageable with said spool to selectably permit removal of said floss from said spool.

7. The dental flossing tool of claim 6 wherein:
said locking means and said spool carry frictionally engageable means for selectably permitting removal of said floss from said spool.

8. The dental flossing tool of claim 7 wherein:
said frictionally engageable means comprise serrated teeth.

9. The dental flossing tool of claim 7 wherein:
said frictionally engageable means is rubber.

10. The dental flossing tool of claim 1 wherein:
said means for feeding said dental floss through said tool without exposure of said floss to air outside of said tool comprises:
a floss dispensing opening formed in one end of said tip to permit said floss to exit from said tip, and
said resilient means mounted within said tip immediately adjacent said floss dispensing opening to prevent moisture and contaminants from passing into said handle portion.

11. The dental flossing tool of claim 10 wherein:
said tip is formed with at least one opening, and
said resilient plug is located between said opening and the rear end of said tip to prevent moisture from entering within said handle portion.

12. The dental flossing tool of claim 1 wherein:
said handle portion is moisture-proof.

13. The dental flossing tool of claim 1 further comprising:
a portion of said handle portion formed to receive said supply of dental floss and being removably attachable to the portion of said tool containing said locking means.

14. The dental flossing tool of claim 1 wherein:
said tool is moisture-proof.

* * * * *